(12) United States Patent
Deisseroth et al.

(10) Patent No.: US 10,369,378 B2
(45) Date of Patent: *Aug. 6, 2019

(54) SYSTEM FOR OPTICAL STIMULATION OF TARGET CELLS

(71) Applicant: The Board of Trustees of the Leland Stanford Junior University, Stanford, CA (US)

(72) Inventors: Karl Deisseroth, Stanford, CA (US); Feng Zhang, Cambridge, MA (US); Edward Boyden, Cambridge, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,895

(22) Filed: Sep. 10, 2018

(65) Prior Publication Data

US 2019/0105510 A1 Apr. 11, 2019

Related U.S. Application Data

(63) Continuation of application No. 15/623,081, filed on Jun. 14, 2017, now Pat. No. 10,105,551, which is a
(Continued)

(51) Int. Cl.
*A61N 1/36* (2006.01)
*A61N 5/06* (2006.01)
(Continued)

(52) U.S. Cl.
CPC ............. *A61N 5/0622* (2013.01); *A61N 1/36* (2013.01); *A61N 5/06* (2013.01); *A61N 5/0601* (2013.01);
(Continued)

(58) Field of Classification Search
CPC .......................... A61N 5/0613; C12N 5/0602
See application file for complete search history.

(56) References Cited

U.S. PATENT DOCUMENTS

| 2,968,302 A | 1/1961 | Fry et al. |
| 3,131,690 A | 5/1964 | Innis et al. |
| (Continued) | | |

FOREIGN PATENT DOCUMENTS

| CN | 1079464 A | 12/1993 |
| CN | 1558222 A | 12/2004 |
| (Continued) | | |

OTHER PUBLICATIONS

Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
(Continued)

*Primary Examiner* — Tuan N Nguyen
(74) *Attorney, Agent, or Firm* — Paula A. Borden; Rudy J. Ng; Bozicevic, Field & Francis LLP

(57) ABSTRACT

Various systems and methods are implemented for controlling stimulus of a cell. One such method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

7 Claims, 4 Drawing Sheets

Specification includes a Sequence Listing.

Related U.S. Application Data continuation of application No. 15/229,064, filed on Aug. 4, 2016, now abandoned, which is a continuation of application No. 14/886,763, filed on Oct. 19, 2015, now abandoned, which is a continuation of application No. 14/665,978, filed on Mar. 23, 2015, now Pat. No. 9,187,745, which is a continuation of application No. 14/219,547, filed on Mar. 19, 2014, now abandoned, which is a continuation of application No. 13/763,119, filed on Feb. 8, 2013, now Pat. No. 8,864,805, which is a continuation of application No. 12/522,520, filed as application No. PCT/US2008/050745 on Jan. 10, 2008, now Pat. No. 8,398,692.

(60) Provisional application No. 60/903,248, filed on Feb. 23, 2007, provisional application No. 60/879,669, filed on Jan. 10, 2007.

(51) Int. Cl.
  C12N 13/00 (2006.01)
  G01N 33/50 (2006.01)
  G01N 33/68 (2006.01)
  C12N 5/071 (2010.01)

(52) U.S. Cl.
  CPC ......... A61N 5/0613 (2013.01); C12N 5/0602 (2013.01); C12N 13/00 (2013.01); G01N 33/502 (2013.01); G01N 33/6872 (2013.01); A61N 2005/0626 (2013.01); A61N 2005/0647 (2013.01); A61N 2005/0652 (2013.01); A61N 2005/0663 (2013.01); A61N 2005/0665 (2013.01)

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,696,722 B2 | 4/2014 | Deisseroth et al. |
| 8,716,447 B2 | 5/2014 | Deisseroth et al. |
| 8,815,582 B2 | 8/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 9,057,734 B2 | 6/2015 | Cohen |
| 9,079,940 B2 | 7/2015 | Deisseroth et al. |
| 9,175,095 B2 | 11/2015 | Deisseroth et al. |
| 9,249,234 B2 | 2/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |

(56) References Cited

U.S. PATENT DOCUMENTS

| | | |
|---|---|---|
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1* | 4/2008 | Schneider ............ A61K 48/005 424/93.21 |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1 | 8/2010 | Hultman et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |

(56) References Cited

U.S. PATENT DOCUMENTS

| | | |
|---|---|---|
| 2011/0125078 A1 | 5/2011 | Denison et al. |
| 2011/0165681 A1 | 7/2011 | Boyden et al. |
| 2011/0166632 A1 | 7/2011 | Delp et al. |
| 2011/0224095 A1 | 9/2011 | Zoller et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1* | 1/2013 | Deisseroth ......... A01K 67/0271 800/8 |
| 2013/0030275 A1 | 1/2013 | Seymour et al. |
| 2013/0066402 A1 | 3/2013 | Lin et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | |
|---|---|---|
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.

Aebischer, et al. "Long-Term Cross-Species Brain Transplantation of a Polymer-Encapsulated Dopamine-Secreting Cell Line", Experimental Neurology, 1991, vol. 111, pp. 269-275.

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

Ahmad, et al. "The *Drosophila rhodopsin* cytoplasmic tail domain is required for maintenance of rhabdomere structure." The FASEB Journal, 2007, vol. 21, p. 449-455.

Airan, et al., "Temporally Precise in vivo Control of Intracellular Signaling", 2009, Nature, vol. 458, No. 7241, pp. 1025-1029.

Airan, et al.; "Integration of light-controlled neuronal firing and fast circuit imaging"; Current Opinion in Neurobiology; vol. 17, pp. 587-592 (2007).

Akirav, et al. "The role of the medial prefrontal cortex-amygdala circuit in stress effects on the extinction of fear", Neural Plasticity, 2007: vol. 2007 Article ID:30873, pp. 1-11.

Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

Alilain, et al.; "Light-Induced Rescue of Breathing after Spinal Cord Injury"; The Journal of Neuroscience; vol. 28, No. 46, pp. 11862-11870 (Nov. 12, 2008).

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Arenkiel, et al. "In vivo light-induced activation of neural circuitry in transgenic mice expressing Channelrhodopsin-2", Neuron, 2007, 54:205-218.

Argos, et al. "The integrase family of site-specific recombinases: regional similarities and global diversity", The EMBO Journal, 1986, vol. 5, No. 2, pp. 433-440.

Asano, et al.; "Optically Controlled Contraction of Photosensitive Skeletal Muscle Cells"; Biotechnology & Bioengineering; vol. 109, No. 1, pp. 199-204 (Jan. 2012).

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Azizgolshani, et al.; "Reconstituted plant viral capsids can release genes to mammalian cells"; Virology; vol. 441, No. 1, pp. 12-17 (2013).

(56) References Cited

OTHER PUBLICATIONS

Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., The use of vectors based on gene amplification for the expression of cloned genes in mammalian cells in "DNA cloning" vol. 3, Academic Press, New York, 1987, pp. 163-188.
Benabid "Future strategies to restore brain functions," Conference proceedings from Medicine Meets Millennium: World Congress of Medicine and Health, 2000, pp. 1-6.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Bibel, et al.; "Differentiation of mouse embryonic stem cells into a defined neuronal lineage"; Nature Neuroscience; vol. 7, No. 9, pp. 1033-1009 (Sep. 2004).
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al.; "A history of optogenetics: the development of tools for controlling brain circuits with light"; F1000 Biology Reports; vol. 3, No. 11, 12 pages (May 3, 2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga Volvox carteri", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow et al., "Optogenetics and translation medicine", Sci Transl Med., 2013, 5(177):177.
Chow, et al.; "High-performance genetically targetable optical neural silencing by light-driven proton pumps"; Nature; vol. 463, pp. 98-102 (Jan. 7, 2010).
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Coleman, et al.; "Assessing Anxiety in Nonhuman Primates"; Ilar Journal; vol. 55, No. 2, pp. 333-346 (2014).
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.

(56) References Cited

OTHER PUBLICATIONS

Cowan et al., "Targeting gene expression to endothelium in transgenic animals: a comparison of the human ICAM-2, PECAM-1, and endoglin promoters", Xenotransplantation, 2003, vol. 10, pp. 223-231.

Crouse, et al. "Expression and amplification of engineered mouse dihydrofolate reductase minigenes" Mol. Cell. Biol. , 1983, vol. 3(2): pp. 257-266.

Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.

Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

Cui, et al., "Electrochemical deposition and characterization of conducting polymer polypyrrole/PSS on multichannel neural probes," Sensors and Actuators, 2001, vol. 93(1): pp. 8-18.

Dalva, et al. "Rearrangements of Synaptic Connections in Visual Cortex Revealed by Laser Photostimulation", Science, 1994,vol. 265, pp. 255-258.

Daniel, et al.; "Stress Modulation of Opposing Circuits in the Bed Nucleus of the Stria Terminalis"; Neuropsychopharmacology Reviews; vol. 41, pp. 103-125 (2016).

Date, et al. "Grafting of Encapsulated Dopamine-Secreting Cells in Parkinson's Disease: Long-Term Primate Study", Cell Transplant, 2000, vol. 9, pp. 705-709.

Davidson, et al.; "Viral Vectors for Gene Delivery to the Nervous System"; Nature Reviews Neuroscience; vol. 4, pp. 353-364 (May 2003).

Davis; "The many faces of epidermal growth factor repeats," The New Biologist; vol. 2, No. 5, pp. 410-419 (1990).

Day, et al.; "The Nucleus Accumbens and Pavlovian Reward Learning"; Neuroscientist; vol. 13, No. 2, pp. 148-159 (Apr. 2007).

De Foubert et al. " Fluoxetine-Induced Change in Rat Brain Expression of Brain-Derived Neurotrophic Factor Varies Depending on Length of Treatment," Neuroscience, 2004, vol. 128, pp. 597-604.

De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).

Dederen, et al. "Retrograde neuronal tracing with cholera toxin B subunit: comparison of three different visualization methods", Histochemical Journal, 1994, vol. 26, pp. 856-862.

Definition of Implant; Merriam-Webster Dictionary; retrieved Nov. 7, 2016 (http://www.merriam-webster.com/dictionary/implant).

Definition of integral. Merriam-Webster Dictionary, retrieved on Mar. 20 2017; Retrieved from the internet: <http://www.merriam-webster.com/dictionary/integral>.

Definition of Psychosis (2015) Wikipedia, retrieved on Feb. 5, 2015 (http://en.wikipedia.org/wiki/psychosis).

Deisseroth "Next-generation optical technologies for illuminating genetically targeted brain circuits," The Journal of Neuroscience, 2006, vol. 26, No. 41, pp. 10380-10386.

Deisseroth et al., "Excitation-neurogenesis Coupling in Adult Neural Stem/Progenitor Cells", 2004, Neuron, vol. 42, pp. 535-552.

Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.

Deisseroth et al., "Signaling from Synapse to Nucleus: the logic Behind the Mechanisms", Currrent Opinion in Neurobiology, 2003, vol. 13, pp. 354-365.

Deisseroth et al., "Translocation of Calmodulin to the Nucleus Supports Creb Phosphorylation in Hippocampal Neurons", Nature, 1998, vol. 392, pp. 198-202.

Deisseroth, et al., "Controlling the Brain with Light", Scientific American, 2010, vol. 303, pp. 48-55.

Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.

Denk, W., et al. "Anatomical and functional imaging of neurons using 2-photon laser scanning microscopy", Journal of Neuroscience Methods, 1994, vol. 54, pp. 151-162.

Deonarain; "Ligand-targeted receptor-mediated vectors for gene delivery"; Exp. Opin. Ther. Patents; vol. 8, No. 1, pp. 53-69 (1998).

Ditterich, et al. "Microstimulation of visual cortex affects the speed of perceptual decisions", 2003, Nature Neuroscience, vol. 6, No. 8, pp. 891-898.

Dittgen, et al. "Lentivirus-based genetic manipulations of cortical neurons and their optical and electrophysiological monitoring in vivo", PNAS, 2004, vol. 101, No. 52, pp. 18206-18211.

Do Carmo, et al.; "Modeling Alzheimer's disease in transgenic rats"; Molecular Neurodegeneration; vol. 8, No. 37, 11 pages (2013).

Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.

Ebert et al., "A Moloney MLV-rat somatotropin fusion gene produces biologically active somatotropin in a transgenic pig", Mol. Endocrinology, 1988, vol. 2, pp. 277-283.

EBI accession No. EMBL: J05199; "N. pharaonis halorhodopsin (hop) gene, complete cds"; (Nov. 22, 1990).

EBI accession No. UNIPROT: A7U0Y6; "SubName: Full=Bacteriorhodopsin"; (Aug. 10, 2010).

EBI accession No. UNIPROT: B0R5N9; "Subname: Full=Bacteriorhodopsin"; (Apr. 8, 2008).

EBI accession No. UNIPROT: B4Y103; "SubName: Full=Channelrhodopsin-1"; (Sep. 23, 2008).

EBI accession No. UNIPROT: P15647; "RecName: Full=Halorhodopsin; Short=HR; Alt Name: Full=NpHR"; (Apr. 1, 1990).

Edelstein, et al.; "Gene therapy clinical trials worldwide 1989-2004—an overview"; The Journal of Gene Medicine; vol. 6, pp. 597-602 (2004).

Ehrlich I. et al. "Amygdala inhibitory circuits and the control of fear memory", Neuron, 2009, vol. 62: pp. 757-771.

Eijkelkamp, et al. "Neurological perspectives on voltage-gated sodium channels", Brain, 2012, 135:2585-2612.

Eisen, "Treatment of amyotrophic lateral sclerosis", Drugs Aging, 1999; vol. 14, No. 3, pp. 173-196.

Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.

Ensell, et al. "Silicon-based microelectrodes for neurophysiology, micromachined from silicon-on-insulator wafers," Med. Biol. Eng. Comput., 2000, vol. 38, pp. 175-179.

Ernst, et al. "Photoactivation of Channelrhodopsin", J. Biol. Chem., 2008, vol. 283, No. 3, pp. 1637-1643.

Esposito et al. "The integrase family of tyrosine recombinases: evolution of a conserved active site domain" , Nucleic Acids Research, 1997, vol. 25, No. 18, pp. 3605-3614.

Evanko "Optical excitation yin and yang" Nature Methods, 2007, 4:384.

Fabian et al. "Transneuronal transport of lectins" Brain Research, 1985, vol. 344, pp. 41-48.

Falconer et al. "High-throughput screening for ion channel modulators," Journal of Biomolecular Screening, 2002, vol. 7, No. 5, pp. 460-465.

Fanselow, et al.; "Why We Think Plasticity Underlying Pavlovian Fear Conditioning Occurs in the Basolateral Amygdala"; Neuron; vol. 23, pp. 229-232 (Jun. 1999).

Farber, et al. "Identification of Presynaptic Neurons by Laser Photostimulation", Science, 1983, vol. 222, pp. 1025-1027.

Feng, et al. "Imaging Neuronal Subsets in Transgenic Mice Expressing Multiple Spectral Variants of GFP", Neuron, 2000, vol. 28, pp. 41-51.

Fenno et al., "The development and application of optogenetics", Annual Review of Neuroscience, 2011, vol. 34, No. 1, pp. 389-412.

(56) References Cited

OTHER PUBLICATIONS

Ferenczi, et al.; "Optogenetic approaches addressing extracellular modulation of neural excitability"; Scientific Reports; vol. 6, 20 pages (Apr. 5, 2016).
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Friedman, et al.; "VTA Dopamine Neuron Bursting is Altered in an Animal Model of Depression and Corrected by Desipramine"; J. Mol. Neurosci.; vol. 34, pp. 201-209 (2008).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gerits, et al.; "Optogenetically Induced Behavioral and Functional Network Changes in Primates"; Current Biology; vol. 22, pp. 1722-1726 (Sep. 25, 2012).
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from Bacillus subtilis DNA" Gene, 1984, vol. 32(1-2): pp. 11-20.
Glick et al."Factors affecting the expression of foreign proteins in Escherichia coli", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gong, et al.; "Enhanced Archaerhodopsin Fluorescent Protein Voltage Indicators"; PLOS One; vol. 8, Issue 6, 10 pages (Jun. 2013).
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat ", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.

Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for Streptomyces phage φBT1 and development of site-specific integrating vectors", Journal of Bacteriology, 2003, vol. 185, No. 17, pp. 5320-5323.
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).

(56) References Cited

OTHER PUBLICATIONS

Han, et al.; "Millisecond-Timescale Optical Control of Neural Dynamics in the Nonhuman Primate Brain"; Neuron; vol. 62, pp. 191-198 (Apr. 30, 2009).
Han, et al.; "Multiple-Color Optical Activation, Silencing, and Desynchronization of Neural Activity with Single-Spike Temporal Resolution", PLoS One, 2007, vol. 2, No. 3, pp. 1-12.
Han, et al.; "Optogenetics in the nonhuman primate"; Prog. Brain Res.; vol. 196, pp. 215-233 (2012).
Han, et al.; "Two-color, bi-directional optical voltage control of genetically-targeted neurons", CoSyne Abstract Presentation, Presented Feb. 24, 2007.
Han, et al.; "Virogenetic and optogenetic mechanisms to define potential therapeutic targets in psychiatric disorders"; Neuropharmacology; vol. 62, pp. 89-100 (2012).
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetlycholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane, " PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Johnson-Saliba, et al.; "Gene Therapy: Optimising DNA Delivery to the Nucleus"; Current Drug Targets; vol. 2, pp. 371-399 (2001).
Johnston et al. "Isolation of the yeast regulatory gene GAL4 and analysis of its dosage effects on the galactose/melibiose regulon," PNAS, 1982, vol. 79, pp. 6971-6975.
Jones, et al.; "Animal Models of Schizophrenia"; British Journal of Pharmacology; vol. 164, pp. 1162-1194 (2011).
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. page S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al. "Diverging neural pathways assemble a behavioural state from separable features in anxiety" Nature, 2013, 496(7444):219-23.

(56) References Cited

OTHER PUBLICATIONS

Kim et al., "Light-Driven Activation of β32-Adrenergic Receptor Signaling by a Chimeric Rhodopsin Containing the β32-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Knopfel, et al.; "A comprehensive concept of optogenetics"; Progress in Brain Research; vol. 196, pp. 1-28 (2012).
Knopfel, et al.; "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "Remote control of cells"; Nature Nanotechnology; vol. 5, pp. 560-561 (Aug. 2010).
Knox, et al.; "Heterologous Expression of *Limulus* Rhodopsin"; The Journal of Biological Chemistry; vol. 278, No. 42, pp. 40493-40502 (Oct. 17, 2003).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kravitz, et al.; "Regulation of parkinsonian motor behaviours by optogenetic control of basal ganglia circuitry"; Nature; vol. 466, No. 622, 8 pages (Jul. 29, 2010).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Bioi. Chem. (2000), 275(16):11597-11602.
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Lin, et al.; "Characterization of Engineered Channelrhodopsin Variants with Improved Properties and Kinetics"; Biophysical Journal; vol. 96, No. 5, pp. 1803-1814 (Mar. 2009).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Luo, et al.; "Synthetic DNA delivery systems"; Nature Biotechnology; vol. 18, pp. 33-37 (Jan. 2000).
Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Maestripieri, et al.; "A modest proposal: displacement activities as an indicator of emotions in primates"; Anim. Behav.; vol. 44, pp. 967-979 (1992).

(56) References Cited

OTHER PUBLICATIONS

Malin et al., "Involvement of the rostral anterior cingulate cortex in consolidation of inhibitory avoidance memory: Interaction with the basolateral amygdala", Neurobiol Learn Mem., Feb. 2007, 87(2):295-302.

Mancuso et al., "Optogenetic probing of functional brain circuitry", Experimental Physiology, 2010, vol. 96.1, pp. 26-33.

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

Mann; "Synapses"; The Nervous System in Action; Chapter 13, http://michaeldmann.net/mann13.html (downloaded Apr. 2014).

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

Masaki, et al.; "β2-Adrenergic Receptor Regulation of the Cardiac L-Type Ca2+ Channel Coexpressed in a Fibroblast Cell Line"; Receptor; vol. 5, pp. 219-231 (1996).

Mattis et al., "Principles for applying optogenetic tools derived from direct comparative analysis of microbial opsins", Nat Methods, 2011, 9(2):159-72.

Mattson, "Apoptosis in Neurodegenerative Disorders", Nature Reviews, 2000, vol. 1: pp. 120-129.

Mayberg et al. "Deep Brain Stimulation for Treatment-Resistant Depression," Focus, 2008, vol. VI, No. 1, pp. 143-154.

Mayford et al., "Control of memory formation through regulated expression of CaMKII transgene", Science, Dec. 1996, 274(5293):1678-1683.

McAllister, "Cellular and Molecular Mechanisms of Dendrite Growth", 2000, Cereb Cortex, vol. 10, No. 10, pp. 963-973.

McKnight "Functional relationships between transcriptional control signals of the thymidine kinase gene of herpes simplex virus", Cell, 1982, vol. 31 pp. 355-365.

Melyan, Z., et al. "Addition of human melanopsin renders mammalian cells Photoresponsive", Nature, 2005, vol. 433: pp. 741-745.

Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.

Meyer, et al. "High density interconnects and flexible hybrid assemblies for active biomedical implants," IEEE Transactions on Advanced Packaging , 2001, vol. 24, No. 3, pp. 366-372.

Milella et al. "Opposite roles of dopamine and orexin in quinpirole-induced excessive drinking: a rat model of psychotic polydipsia'" Psychopharmacology, 2010, 211:355-366.

Monje et al., "Irradiation Induces Neural Precursor-Cell Dysfunction", Natural Medicine, 2002, vol. 8, No. 9, pp. 955-962.

Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.

Mortensen et al. "Selection of Transfected Mammalian Cells," Supplement 86, Current Protocols in Molecular Biology, 1997, 9.5.1-09.5.19.

Mourot et al., "Rapid Optical Control of Nociception with an Ion Channel Photoswitch", Nat Methods, 2012, 9(4):396-402.

Mueller, et al.; "Clinical Gene Therapy Using Recombinant Adeno-Associated Virus Vectors"; Gene Therapy; vol. 15, pp. 858-863 (2008).

Mullins et al., "Expression of the DBA/2J Ren-2 gene in the adrenal gland of transgenic mice", EMBO, 1989, vol. 8, pp. 4065-4072.

Mullins et al., "Fulminant hypertension in transgenic rats harbouring the mouse Ren-2 gene", Nature, 1990, vol. 344, pp. 541-544.

Nacher, et al. "NMDA receptor antagonist treatment increases the production of new neurons in the aged rat hippocampus", Neurobiology of Aging, 2003,vol. 24, No. 2: pp. 273-284.

Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.

Nagel, et al. "Channelrhodopsin-I: a light-gated proton channel in green algae", Science, 2002, vol. 296: pp. 2395-2398.

Nagel, et al. "Channelrhodopsin-2, a directly light-gated cation-selective membrane channel", PNAS, 2003, vol. 100, No. 24: pp. 13940-13945.

Nakagami, et al. "Optical Recording of Trisynaptic Pathway in Rat Hippocampal Slices with a Voltage-Sensitive Dye" Neuroscience, 1997, vol. 81, No. 1, pp. 1-8.

Naqvi, et al. "Damage to the insula disrupts addiction to cigarette smoking," Science; 2007, vol. 315 pp. 531-534.

Natochin, et al. "Probing rhodopsin-transducin interaction using *Drosophila* Rh1-bovine rhodopsin chimeras," Vision Res., 2006, vol. 46, No. 27: pp. 4575-4581.

Nelson, et al.; "Non-Human Primates: Model Animals for Developmental Psychopathology": Neuropsychopharmacology; vol. 34, No. 1, pp. 90-105 (Jan. 2009).

Nieh et al., "Optogenetic dissection of neural circuits underlying emotional valence and motivated behaviors", Brain Research, E-pub 2012, 1511:73-92.

Nirenberg, et al. "The Light Response of Retinal Ganglion Cells is Truncated by a Displaced Amacrine Circuit", Neuron, 1997, vol. 18: pp. 637-650.

No Authors Listed; "Two bright new faces in gene therapy," Nature Biotechnology, 1996, vol. 14: p. 556.

Nonet, "Visualization of synaptic specializations in live C. elegans with synaptic vesicle protein-GFP fusions", J. Neurosci. Methods, 1999, 89:33-40.

Nunes-Duby, et al. "Similarities and differences among 105 members of the Int family of site-specific recombinases" , Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.

Ory, et al. "A stable human-derived packaging cell line for production of high titer retrovirus/vesicular stomatitis virus G pseudotypes," PNAS, 1996, vol. 93: pp. 11400-11406.

Packer, et al.; "Targeting Neurons and Photons for Optogenetics"; Nature Neuroscience; vol. 16, No. 7, pp. 805-815 (Jul. 2013).

Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

Palmer et al., "The Adult Rat Hippocampus Contains Primordial Neural Stem Cells", Molecular and Cellular Neuroscience, 1997, vol. 8, pp. 389-404.

Palu, et al.; "In pursuit of new developments for gene therapy of human diseases"; Journal of Biotechnology; vol. 68, pp. 1-13 (1999).

Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.

Panda, et al. "Illumination of the Melanopsin Signaling Pathway", Science, 2005, vol. 307: pp. 600-604.

Pandya, et al.; "Where in the Brain Is Depression?"; Curr. Psychiatry Rep.; vol. 14, pp. 634-642 (2012).

Pape, et al., "Plastic Synaptic Networks of the Amygdala for the Acquisition, Expression, and Extinction of Conditioned Fear", 2010, Physiol Rev, vol. 90, pp. 419-463.

Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.

Pear "Transient Transfection Methods for Preparation of High-Titer Retroviral Supernatants" Supplement 68, Current Protocols in Molecular Biology, 1996, 9.1 1 .1-9.1 1 .I8.

(56) References Cited

OTHER PUBLICATIONS

Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.

Peterlin, et al. "Optical probing of neuronal circuits with calcium indicators," PNAS, 2000, vol. 97, No. 7: pp. 3619-3624.

Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.

Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).

Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.

Pettit, et al. "Local Excitatory Circuits in the Intermediate Gray Layer of the Superior Colliculus", J Neurophysiol., 1999, vol. 81, No. 3: pp. 1424-1427.

Pfeifer, et al.; "Gene Therapy: Promises and Problems"; Annu. Rev. Genomics Hum. Genet.; vol. 2, pp. 177-211 (2001).

Pinkham et al., "Neural bases for impaired social cognition in schizophrenia and autism spectrum disorders", Schizophrenia Research, 2008, vol. 99, pp. 164-175.

Potter, "Transfection by Electroporation." Supplement 62, Current Protocols in Molecular Biology, 1996, 9.3.1-9.3.6.

Pouille, et al. "Routing of spike series by dynamic circuits in the hippocampus", Nature, 2004, vol. 429: pp. 717-723.

Powell, et al.; "Schizophrenia-Relevant Behavioral Testing in Rodent Models: A Uniquely Human Disorder?"; Biol. Psychiatry; vol. 59, pp. 1198-1207 (2006).

Qiu et al. "Induction of photosensitivity by heterologous expression of melanopsin", Nature, 2005, vol. 433: pp. 745-749.

Racaniello; "How many viruses on Earth?"; Virology Blog; 6 pages; http://www.virology.ws/2013/09/06/how-many-viruses-on-earth/ (Sep. 6, 2013).

Ramalho, et al.; "Mouse genetic corneal disease resulting from transgenic insertional mutagenesis"; Br. J. Ophthalmol.; vol. 88, No. 3, pp. 428-432 (Mar. 2004).

Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Randic, et al. "Long-term Potentiation and Long-term Depression of Primary Afferent Neurotransmission in the Rat Spinal Cord", 1993, Journal of Neuroscience, vol. 13, No. 12, pp. 5228-5241.

Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).

Rathnasingham et al., "Characterization of implantable microfabricated fluid delivery devices," IEEE Transactions on Biomedical Engineering, 2004, vol. 51, No. 1: pp. 138-145.

Rein, et al., "The Optogenetic (r)evolution", Mol. Genet. Genomics, 2012, vol. 287, No. 2, pp. 95-109.

Remy, et al., "Depression in Parkinson's Disease: Loss of Dopamine and Noradrenaline Innervation in the Limbic System", Brain, 2005, vol. 128 (Pt 6), pp. 1314-1322.

Ristevski; "Making Better Transgenic Models: Conditional, Temporal, and Spatial Approaches"; Molecular Biotechnology; vol. 29, No. 2, pp. 153-163 (Feb. 2005).

Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.

Rivera et al., "BDNF-Induced TrkB Activation Down-Regulates the K+-Cl− cotransporter KCC2 and Impairs Neuronal Cl− Extrusion", The Journal of Cell Biology, 2002, vol. 159: pp. 747-752.

Rogers, et al.; "Effects of ventral and dorsal CA1 subregional lesions on trace fear conditioning"; Neurobiology of Learning and Memory; vol. 86, pp. 72-81 (2006).

Rosenkranz, et al. "The prefrontal cortex regulates lateral amygdala neuronal plasticity and responses to previously conditioned stimuli", J. Neurosci., 2003, vol. 23, No. 35: pp. 11054-11064.

Rousche, et al., "Flexible polyimide-based intracortical electrode arrays with bioactive capability," IEEE Transactions on Biomedical Engineering, 2001, vol. 48, No. 3, pp. 361-371.

Rubinson et at. "A lentivirus-based system to functionally silence genes in primary mammalian cells, stem cells and transgenic mice by RNA interference," Nature Genetics, 2003, vol. 33, p. 401-406.

Rudiger et at. "Specific arginine and threonine residues control anion binding and transport in the light-driven chloride pump halorhodopsin," The EMBO Journal, 1997, vol. 16, No. 13, pp. 3813-3821.

Sajdyk, et al., "Excitatory Amino Acid Receptors in the Basolateral Amygdala Regulate Anxiety Responses in the Social Interaction Test", Brain Research, 1997, vol. 764, pp. 262-264.

Salzman, et al."Cortical microstimulation influences perceptual judgements of motion direction", Nature, 1990, vol. 346, pp. 174-177.

Samuelson; "Post-traumatic stress disorder and declarative memory functioning: a review"; Dialogues in Clinical Neuroscience; vol. 13, No. 3, pp. 346-351 (2011).

Santana et al., "Can Zebrafish Be Used as Animal Model to Study Alzheimer's Disease?" Am. J. Neurodegener. Dis. (2012), 1(1):32-48.

Sato et al. "Role of Anion-binding Sites in cytoplasmic and extracellular channels of *Natronomonas pharaonis* halorhodopsin," Biochemistry, 2005. vol. 44, pp. 4775-4784.

Sauer "Site-specific recombination: developments and applications," Current Opinion in Biotechnology, 1994, vol. 5, No. 5: pp. 521-527.

Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).

Schiff, et al. "Behavioral improvements with thalamic stimulation after severe traumatic brain injury," Nature, 2007, vol. 448, pp. 600-604.

Schlaepfer et al. "Deep Brain stimulation to Reward Circuitry Alleviates Anhedonia in Refractory Major Depresion," Neuropsychopharmacology, 2008,vol. 33, pp. 368-377.

Schroll et al., "Light-induced activation of distinct modulatory neurons triggers appetitive or aversive learning in drosophila larvae", Current Biology, Sep. 2006, 16(17):1741-1747.

Sclimenti, et al. "Directed evolution of a recombinase for improved genomic integration at a native human sequence," Nucleic Acids Research, 2001, vol. 29, No. 24: pp. 5044-5051.

Sheikh et al., "Neurodegenerative Diseases: Multifactorial Conformational Diseases and Their Therapeutic Interventions", Journal of Neurodegenerative Diseases (2013), Article ID 563481:1-8.

Shepherd, et al. "Circuit Analysis of Experience-Dependent Plasticity in the Developing Rat Barrel Cortex", Neuron, 2003, vol. 38: pp. 277-289.

Shibasaki et al., "Effects of body temperature on neural activity in the hippocampus: Regulation of resting membrane potentials by transient receptor potential vanilloid 4," The Journal of Neuroscience, 2007, 27(7):1566-1575.

Shimizu, et al.; "NMDA Receptor-Dependent Synaptic Reinforcement as a Crucial Process for Memory Consolidation"; Science; vol. 290, pp. 1170-1174 (Nov. 10, 2000).

Shoji, et al.; "Current Status of Delivery Systems to Improve Target Efficacy of Oligonucleotides"; Current Pharmaceutical Design; vol. 10, pp. 785-796 (2004).

Sigmund; "Viewpoint: Are Studies in Genetically Altered Mice Out of Control?"; Arterioscler Thromb Vasc Biol.; vol. 20, No, 6, pp. 1425-1429 (Jun. 2000).

(56) References Cited

OTHER PUBLICATIONS

Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtii", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Smith, et al.; "Proton binding sites involved in the activation of acid-sensing ion channel ASIC2a"; Neuroscience Letters; vol. 426, pp. 12-17 (2007).
Sofuoglu, et al.; "Cholinergic Functioning in Stimulant Addiction: Implications for Medications Development"; CNS Drugs; vol. 23, No. 11, pp. 939-952 (Nov. 1, 2009).
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Steimer; "The biology of fear- and anxiety-related behaviors"; Dialogues in Clinical Neuroscience; vol. 4, No. 3, pp. 231-249 (Sep. 2002).
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Stuber; "Dissecting the neural circuitry of addiction and psychiatric disease with optogenetics"; Neuropsychopharmacology; vol. 35, No. 1, pp. 341-342 (2010).
Suzuki et al. "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the Cooh Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Tennesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tsuchida; "Nervous Control of Micturition"; The Japanese Journal of Urology; vol. 80, No. 9, pp. 1257-1277 (1989).
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Uniprot Accession No. P02945, integrated into the database on Jul. 21, 1986.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-38.
Vanin, et al. "Development of high-titer retroviral producer cell lines by using Cre-mediated recombination," Journal of Virology, 1997, vol. 71, No. 10: pp. 7820-7826.

(56) References Cited

OTHER PUBLICATIONS

Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (Mini) Probe System," Proceedings of the 2005 IEEE, Engineering in Medicine and Biology 27th Annual Conference, Shanghai, China, Sep. 1-4, 2005, pp. 7341-7344.
Wagner, "Noninvasive Human Brain Stimulation", Annual Rev. Biomed. Eng. 2007. 9:I9.1-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No., 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Weiss, et al.; "Galanin: A Significant Role in Depression?"; Annals New York Academy of Sciences; vol. 863, No. 1, pp. 364-382 (1998).
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330: 17 pages.
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Written opinion of PCT Application No. PCT/US2011/059383 (dated May 9, 2012).

Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human $\beta,\beta$-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.

(56) References Cited

OTHER PUBLICATIONS

Duvarci, et al "The bed Nucleaus of the Stria Terminalis Mediates inter-individual variations in anxiety and fear", J. Neurosci., 29(33) 10357-10361 (2009).
Matsuda "Bed nucleus of stria terminalis (BNST)" Benshi Seishin Igaku (Molecular Psychiatric Medicine), 2009, vol. 9 No. 3, p. 46-49.
Neuropsychopharmacology, 2011, vol. 36 No. Suppl.1, p. S110 (Abstract No. 67).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).
Belzung et al., "Optogenetics to study the circuits of fear- and depresssion-like behaviors: A critical analysis," Pharmacology, Biochemistry and Behavior, 2014, 122: 144-157.
Bernstein & Boyden "Optogenetic tools for analyzing the neural circuits of behavior," Trends Cogn Sci., 2011, 15(12): 592-600.
Erbguth et al. "Bimodal Activation of Different Neuron Classes with Spectrally Red-Shifted Channelrhodopsin Chimera C1V1 in Caenorhabditis elegans," PLOS ONE, 2012, vol. 7 No. 10, pp. e46827/1-9.
Li et al.; "Role of a Helix B Lysine Residue in the Photoactive Site in Channelrhodopsins," Biophysical Journal, 2014, vol. 106, pp. 1607-1617.
Prigge et al.: "Functional Studies of Volvox Channelrhodopsin Chimeras," Biophysical Journal, 2010, vol. 98, No. 3, Suppl. 1, 3694 Poster, 1 page.
Prigge et al.; Color-tuned Channelrhodopsins for Multiwavelength Optogenetics, J. Biol. Chem. 2012, vol. 287, No. 38, pp. 31804-31812.
Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.
Nargeot et al.; Molecular basis of the diversity of calcium channels in cardiovascular tissues European Heart Journal, 1997, Supplemental A, A15-A26.

* cited by examiner

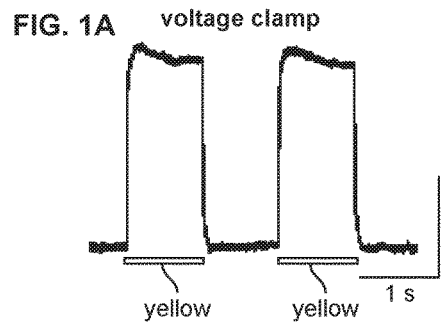
FIG. 1A
FIG. 1B
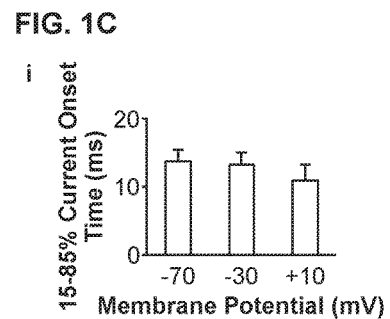
FIG. 1C
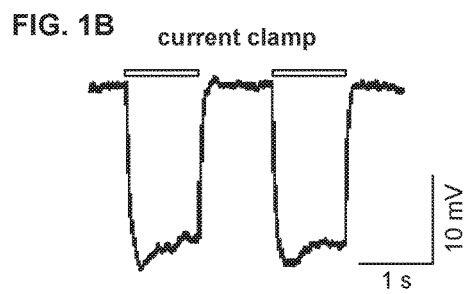
FIG. 1D
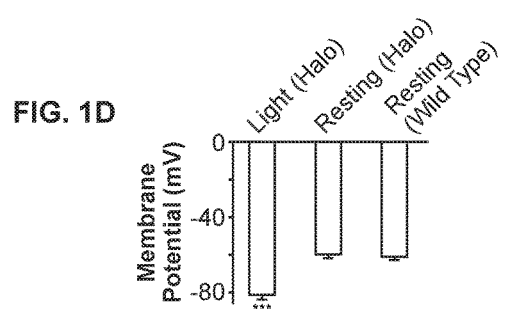
FIG. 1E
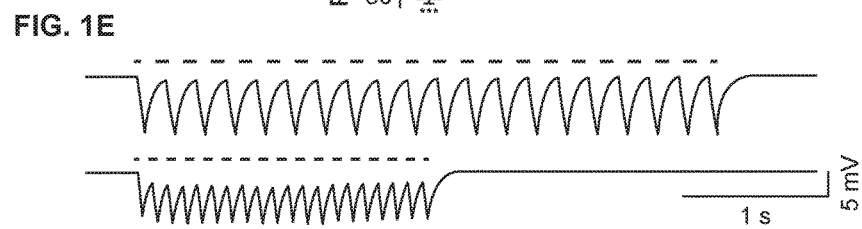

Time (s)

SEQUENCE LISTING

<160> NUMBER OF SEQ ID NOS: 5

<210> SEQ ID NO 1
<211> LENGTH: 876
<212> TYPE: DNA
<213> ORGANISM: Artificial Sequence
<220> FEATURE:
<223> OTHER INFORMATION: mammalian codon-optimized sequence from
      Natronobacterium pharaonis

<400> SEQUENCE: 1

| | | | | | | |
|---|---|---|---|---|---|---|
| atgactgaga | ccctcccacc | cgtgactgaa | agcgccgtcg | ctctgcaagc | agaggttacc | 60 |
| cagcgggagc | tgttcgagtt | cgtcctcaac | gaccccctcc | tggcttctag | cctctacatc | 120 |
| aacattgctc | tggcaggcct | gtctatactg | ctgttcgtct | tcatgaccag | gggactcgat | 180 |
| gaccctaggg | ctaaactgat | tgcagtgagc | acaattctgg | ttcccgtggt | ctctatcgct | 240 |
| tcctacactg | ggctggcatc | tggtctcaca | atcagtgtcc | tggaaatgcc | agctggccac | 300 |
| tttgccgaag | ggagttctgt | catgctggga | ggcgaagagg | tcgatggggt | tgtcacaatg | 360 |
| tggggtcgct | acctcacctg | ggctctcagt | accccatga | tcctgctggc | actcggactc | 420 |
| ctggccggaa | gtaacgccac | caaactcttc | actgctatta | cattcgatat | cgccatgtgc | 480 |
| gtgaccgggc | tcgcagctgc | cctcaccacc | agcagccatc | tgatgagatg | gttttggtat | 540 |
| gccatctctt | gtgcctgctt | tctggtggtg | ctgtatatcc | tgctggtgga | gtgggctcag | 600 |
| gatgccaagg | ctgcagggac | agccgacatg | tttaatacac | tgaagctgct | cactgtggtg | 660 |
| atgtggctgg | gttaccctat | cgtttgggca | ctcggcgtgg | agggaatcgc | agttctgcct | 720 |
| gttggtgtga | caagctgggg | ctactccttc | ctggacattg | tggccaagta | tattttgcc | 780 |
| tttctgctgc | tgaattatct | gacttccaat | gagtccgtgg | tgtccggctc | catactggac | 840 |
| gtgccatccg | ccagcggcac | acctgccgat | gactga | | | 876 |

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
gaattcgcca ccatgactga gaccctccca cccgtg         36

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
ggatccgtca tcggcaggtg tgccgctggc         30

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ccggtgccac catgactgag accctcccac ccgtg         35

```
<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
gaattcttac ttgtacagct cgtccatcgg                                        30
```

SYSTEM FOR OPTICAL STIMULATION OF TARGET CELLS

RELATED PATENT DOCUMENTS

This application is a continuation of U.S. patent application Ser. No. 15/623,081, filed Jun. 14, 2017, now U.S. Pat. No. 10,105,551, which is a continuation of U.S. patent application Ser. No. 15/229,064, filed Aug. 4, 2016, which is a continuation of U.S. patent application Ser. No. 14/886,763, filed Oct. 19, 2015, which is a continuation of U.S. patent application Ser. No. 14/665,978, filed Mar. 23, 2015, now U.S. Pat. No. 9,187,745, which is a continuation of U.S. patent application Ser. No. 14/219,547, filed Mar. 19, 2014, which is a continuation of U.S. patent application Ser. No. 13/763,119, filed Feb. 8, 2013, now U.S. Pat. No. 8,864,805, which is a continuation of U.S. patent application Ser. No. 12/522,520, filed Jan. 8, 2010, now U.S. Pat. No. 8,398,692, which is a U.S. national phase filing under 35 U.S.C. § 371 of PCT/US2008/050745, filed Jan. 10, 2008, which application claims benefit under 35 U.S.C. § 119(e) both of U.S. Provisional Application No. 60/879,669 filed on Jan. 10, 2007 and entitled "Genetically-Targetable Optical Inactivation of Excitable Cells" and of U.S. Provisional Application No. 60/903,248 filed on Feb. 23, 2007 and entitled "Genetically-Targetable Optical Inactivation of Excitable Cells," each of which applications is fully incorporated herein by reference.

FIELD OF THE INVENTION

The present invention relates generally to systems and approaches for stimulating target cells, and more particularly, to using optics to dissuade stimulation-generated pulse trains.

BACKGROUND

Various efforts in neuroscience are directed towards determining whether neural activity in a specific brain region, or in a set of genetically-identified neurons, contributes to a particular neural computation, behavior, or neurological or psychiatric disorder. For centuries, insights have come from studies of human patients with specific lesions, as exemplified by Paul Broca's delineation in the 1860s of the eponymous brain area that, when dysfunctional, results in deficits of speech production. Many studies have used ablation or pharmacological shutdown of neurons or brain regions in animals, or careful analysis of patients, to parse out the physical substrates of normal and abnormal behavior. However, growing awareness that activity in multiple brain regions may be coordinated during performance of a behavior, or in a particular neural dysfunction, has raised the question of precisely when specific brain regions or neurons contribute. For example, a large number of in vivo recording studies have demonstrated, for many brain regions, that specific neurons can fire action potentials during precise intervals within a behavioral task. The intervals can last as little as a fraction of a second; it is possible that specific brain regions or neurons are required only at specific times in a task, not continuously. In humans, use of transcranial magnetic stimulation to disrupt the visual cortex has demonstrated that conscious perception requires intact cortical performance during temporal windows that last tens of milliseconds, occurring at precise times after visual stimulus presentation. Accordingly, a method for disrupting activity in targeted cell types for very precisely delimited periods of time (e.g., several milliseconds) could help answer a number of outstanding questions, and enable novel ones to be asked. For example, one question involves the identification of the precise brain regions, cell types, and activity patterns required at each phase (sensory, decision-making and motor) of a behavioral task. Another question involves, for a particular perception (e.g., feeling, decision, memory, or action) identifying the precise number of neurons that must be active within a certain region and how long the neurons are active. Another question involves the identification of the causal role of neural synchrony and precise spike timing in neural computation, plasticity, and pathological brain function. As memories are encoded, consolidated, and forgotten, it can be important to identifying how the critical neural loci of memory changes.

SUMMARY

The claimed invention is directed to photosensitive biomolecular structures and related methods. The present invention is exemplified in a number of implementations and applications, some of which are summarized below.

According to one example embodiment of the present invention, a method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which:

FIG. 1A shows sample outward currents elicited by two pulses of yellow light in a voltage-clamped neuron, consistent with an embodiment of the present invention;

FIG. 1B shows sample membrane voltage hyperpolarizations elicited by two pulses of yellow light, in a current-clamped neuron held at resting membrane potential, consistent with an embodiment of the present invention;

FIG. 1C shows Kinetic properties of yellow light-elicited, Halo-mediated currents from voltage-clamped neurons, consistent with an embodiment of the present invention;

FIG. 1D shows membrane potentials of neurons expressing Halo-GFP and exposed to yellow light, neurons expressing Halo-GFP but not exposed to any light, and neurons without transfection with Halo-GFP, consistent with an embodiment of the present invention;

FIG. 1E shows sample membrane hyperpolarizations induced by 5 Hz and 10 Hz trains of yellow light pulses, consistent with an embodiment of the present invention;

Figure 2A:
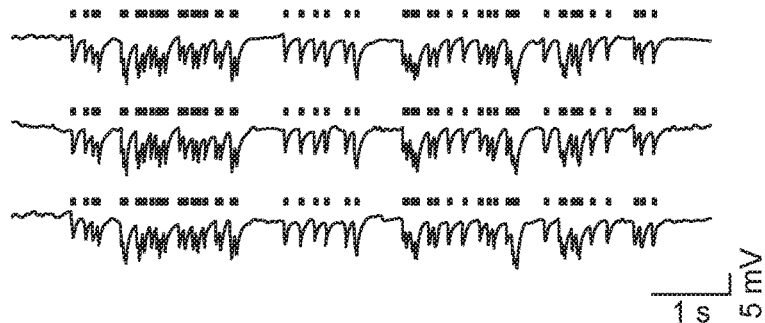
FIG. 2A shows three voltage traces of a current-clamped hippocampal neuron, exposed to a Poisson train of yellow light pulses, consistent with an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of photosensitive biomolecular structures, and the invention has been found to be particularly suited for use in arrangements and methods dealing with neuron stimulation. While the present invention is not necessarily limited to such applications, various aspects of the invention may be appreciated through a discussion of various examples using this context.

The aspects of the present invention are directed to a technology that enables rapid neural inactivation and release from inactivation at the millisecond timescale, is safe and effective, has minimal effects on cellular physiology or survival, and requires no exogenous chemicals to be delivered. A specific embodiment of the invention involves a single-component protein capable of mediating light-induced inhibition, the mammalian codon-optimized version of the light-driven chloride pump halorhodopsin, from the archaebacterium *Natronobacterium pharaonic* (abbreviated Halo). Although such halobacteria are known to live in very high saline concentrations (e.g., >1 M), some wild-type halorhodopsins have been shown to preserve functionality at much lower chloride concentrations, even at levels comparable to those found in mammalian cerebrospinal fluid. Applications of the present invention involve the use of Halo to mediate optical inhibition of neuronal spiking in a physiologically accurate milieu, in response to pulses of somatically injected intracellular current (~300 PA), with temporal onset and offset of inhibition in the range of 10-15 milliseconds. Moreover, Halo can mediate naturalistic trains of inhibitory voltage changes at physiologically relevant frequencies, with minimal attenuation of voltage amplitude from pulse to pulse.

Aspects of an embodiment of the invention are also directed to a single neuron expressing both Halo and the blue-light driven cation channel Channelrhodopsin-2 (ChR2), neural inhibition and excitation are controlled at the millisecond timescale by pulses of yellow and blue light, respectively. In one instance, these channels provide the capability to create lesions of virally or transgenically targeted neural circuits over precise timescales, as well as neuroengineering interfaces for bi-directional control of excitable cell depolarization and hyperpolarization.

One embodiment of the present invention involves a designed fusion protein having the mammalian codon-optimized form of *N. pharaonis* halorhodopsin (Halo), with EGFP added in-frame at the C-terminus for ease of visualization. When expressed using the CaMKII promoter, which targets excitatory neurons of the forebrain, Halo-EGFP fluoresced brightly and appeared evenly distributed in the neuron. When exposed to ~10 m W/mm$^2$ yellow light (e.g., from a xenon lamp, filtered by a standard Texas red excitation filter (bandpass, 560±27.5 nm, Chroma), voltage-clamped hippocampal neurons expressing Halo can experience outward currents with rapid onset, stable steady-state, and abrupt shut-off with cessation of illumination. In some instances, no supplementation of the culture medium or the recording medium with the halorhodopsin cofactor all-trans retinal is necessary. This is believed to be due to levels of all-trans retinal naturally occurring in mammalian neurons in culture and in live brain that are high enough to enable type I opsins without chemical supplementation.

FIG. 1 shows the results of an experimental test of millisecond-timescale, yellow light-driven, neuronal hyperpolarization with Halo. A cultured hippocampal neuron expressing mammalian codon-optimized *N. pharaonic* halorhodopsin (Halo) fused to GFP under the CaMKII promoter is used.

FIG. 1A shows sample outward currents elicited by two 1-second pulses of yellow (560±27.5 nm) light (~10 mW/mm$^2$) in a voltage-clamped neuron held at −70 mV. Yellow bars in this and subsequent figures indicate the period of yellow light exposure.

FIG. 1C shows Kinetic properties of yellow light-elicited, Halo-mediated currents from voltage-clamped neurons. FIG. 1Ci shows 15-85% current onset time. FIG. 1Cii shows 85-15% offset time. For each measurement, data is presented from neurons held at −70 mV (n=14 neurons), −30 mV (n=10), and +10 mV (n=10) (left to right). Bars represent mean±standard error of the mean (S.E.M.).

FIG. 1B shows sample membrane voltage hyperpolarizations elicited by two 1-second pulses of yellow light, in a current-clamped neuron held at resting membrane potential.

FIG. 1D shows membrane potentials of neurons expressing Halo-GFP and exposed to yellow light (left, n=14), expressing Halo-GFP but not exposed to any light (middle, n=11), and without transfection with Halo-GFP (right, n=8). *** denotes significant difference between the Halo-GFP+ light condition and each of the other two conditions (p<0.0001; Fisher's partial least-squares difference (PLSD) post hoc test after ANOVA).

FIG. 1E shows sample membrane hyperpolarizations induced by 5 Hz (top) and 10 Hz (bottom) trains of yellow light pulses, with light pulse durations of 50 ms (top) and 25 ms (bottom), respectively.

In related experimental tests, the light pulses elicited pulse amplitudes of 56.9±23.4 pA (mean±st. dev.; n=14 neurons). Repeating a 1-second pulse of yellow light twice, spaced by 1 second in darkness, resulted in identical pulse amplitudes each time (p>0.50, paired t-test), as shown in FIG. 1A.

This stable current amplitude appears to be consistent with what is known about the halorhodopsin photocycle. As befits a chloride pump, the current amplitude did not vary significantly with holding voltage (F=0.004, p>0.95, ANOVA with factor of holding voltage), nor did any measured kinetic parameters vary, such as the onset or offset times of the current pulses (F<0.6, p>0.55 for all comparisons, ANOVA; FIG. 1C). The onset and offset times of elicited currents were seen to be on the order ~10-15 ms at all holding voltages tested. This suggests that Halo is a viable candidate for ultratransient shutdown of spike trains (FIG. 1Ci, 1Cii). When held in current clamp, hippocampal neurons underwent peak hyperpolarizations of −21.6±11.3 mV (mean±st. dev.; n=11 neurons) in response to pulses of yellow light, with no difference between the peak hyperpolarizations achieved by two pulses separated by a 1-second pause (p>0.85, paired t-test; FIG. 1B). These large voltage changes were relatively rapid, with onset and offset times of 68±57 and 73±39 ms, respectively. Thus, Halo has been shown to be capable of reliably mediating hyperpolarizations of significant magnitude, with fast onset and offset times at the beginning and end of light exposure.

Several control experiments were implemented to evaluate whether Halo has unanticipated side effects, such as altering basal cell physiology or increasing the propensity for cell death. First, the basal state of Halo-expressing neurons electrophysiologically was characterized when no light was present. When measured in darkness, no difference was seen between the resting potentials of neurons expressing Halo and those of neighboring neurons in the culture that were untransfected (p>0.20, n=11 Halo-positive cells, n=8 Halo-negative cells; FIG. 1D). This result suggests that basal neural activity would be little affected by the presence of Halo. On the other hand, Halo-expressing neurons illuminated with yellow light were significantly hyperpolarized, with respect to both Halo-expressing neurons in darkness and non-transfected cells (p<0.0001 for both of these comparisons, Fisher's partial least squares difference post hoc test after ANOVA (F=28.4, p<0.0001) with factor of experimental condition; FIG. 1D). An independent assay for unanticipated effects on cell health, the membrane-impermeant DNA stain ethidium homodimer-1 was used to detect the cell membrane breakdown accompanying cell death for one week in Halo-expressing cells. Little difference was found in the prevalence of cell death between Halo-positive and Halo-negative neurons: 16/308 (5.2%) non-transfected neurons counted, and 1/22 (4.5%) Halo-expressing neurons counted, were labeled by ethidium homodimer-1, indicating that Halo was not toxic over the course of the one-week experiment (x2=0.02, p>0.85).

In an effort to explore the uses Halo could present in the analysis and engineering of intact neural circuits, an experiment was performed to determine whether the fast response times of Halo could support naturalistic sequences of hyperpolarization events, in response to trains of brief pulses of yellow light.

FIG. 2 shows high-fidelity Halo-mediated naturalistic trains of inhibitory events. FIG. 2A shows three voltage traces of a current-clamped hippocampal neuron, exposed to a Poisson train of yellow light pulses. Each light pulse lasts 10 ms, and the Poisson train has a mean inter-pulse interval of λ=100 ms.

Figure 2B:
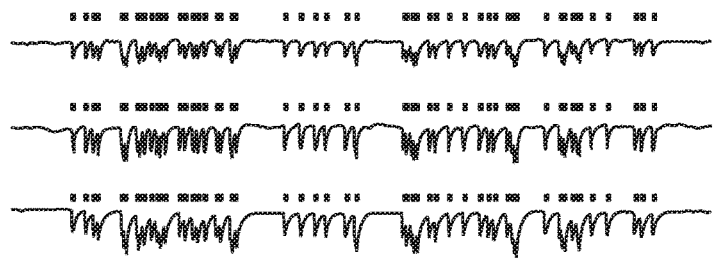
FIG. 2B shows voltage traces of three different current-clamped neurons exposed to the same Poisson train of light pulses ($\lambda$=100 ms), consistent with an embodiment of the present invention.

FIG. 2B shows voltage traces of three different current-clamped neurons exposed to the same Poisson train of light pulses (λ=100 ms).

Figure 2C:
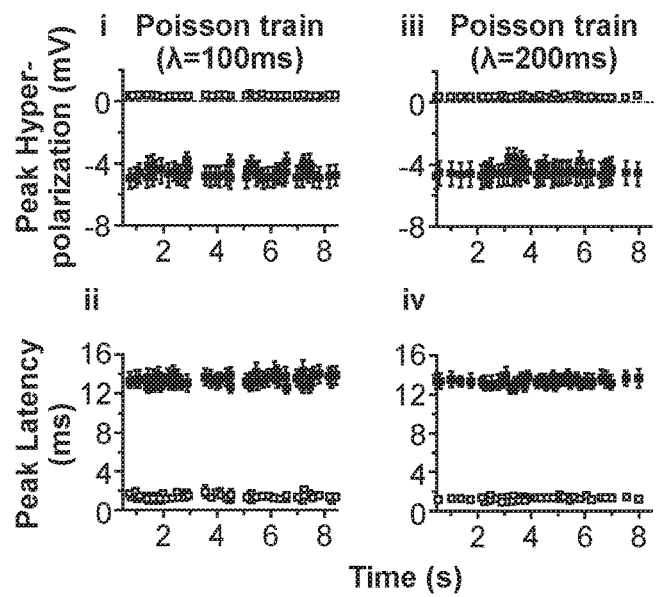
FIG. 2C shows properties of hyperpolarization events elicited by Poisson trains with various inter-pulse intervals, consistent with an embodiment of the present invention.

FIG. 2C shows properties of hyperpolarization events elicited by Poisson trains with inter-pulse interval λ=100 ms (i, ii) and λ=200 ms (iii, iv), plotted versus onset time of each light pulse. Plots (i) and (iii) show the peak of each hyperpolarization event, as well as the across-trials standard deviation of these amplitude values across ten trials. Plots (ii) and (iv) show the latency between the onset time of the light pulse and the time of the hyperpolarization peak, as well as the across-trials standard deviation of these timing values across ten trials. All plotted points are across-neuron mean±S.E.M. (n=5 neurons).

Figure 2D:
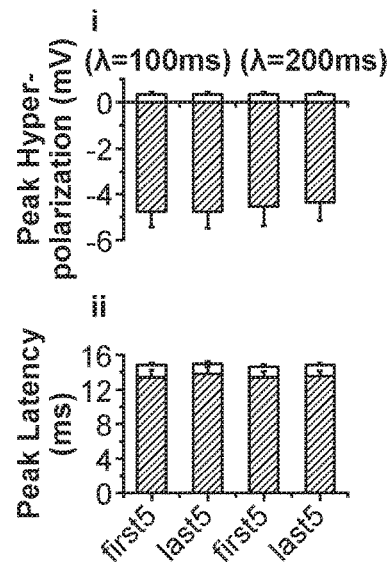
FIG. 2D shows a comparison of the peak hyperpolarization and the time-to-peak data at the beginning and end of the Poisson trains, for the neurons described in FIG. 2C, consistent with an embodiment of the present invention.

FIG. 2D shows a comparison of the peak hyperpolarization (i) and the time-to-peak (ii) data at the beginning (first 5) and end (last 5) of the λ=100 ms and λ=200 ms Poisson trains, for the n=5 neurons described in FIG. 2C. In (i): for each neuron, the average of the first 5 or last 5 hyperpolarization peaks or the across-trials standard deviation of these amplitude values was first computed, then the across-neuron mean±S.E.M. was plotted. In (ii): for each neuron, the average of the first 5 or last 5 times-to-peak or the across-trials standard deviation of these times-to-peak were first computed, then the across-neuron mean±S.E.M. was plotted.

FIG. 2A shows three traces of hyperpolarization events elicited in a single neuron, resulting from repeatedly playing back a Poisson train (mean inter-pulse interval, λ=100 ms, 59 pulses), of 10 ms-duration yellow light pulses, to simulate stochastic synaptic inhibitory input. FIG. 2B shows three such hyperpolarization traces, taken from different neurons. The variability of such trains was remarkably low in many regards—across ten repeated trials in a single cell, across multiple cells (n=5 neurons), and over time throughout a sustained train of 59 pulses (FIG. 2C, 2D). It was found that for hyperpolarizations elicited by 10 ms-duration light pulses during a λ=100 ms Poisson train, the mean amplitude was −4.56 mV (averaged across trials and neurons), but the trial-to-trial standard deviation of this amplitude was only 0.40 mV (averaged across neurons, FIG. 2Ci and FIG. 2Di). The trial-to-trial jitter of the time the hyperpolarization took to reach its peak value was also small, 1.27 ms (averaged across neurons, FIG. 2Cii and FIG. 2Dii). The neuron-to-neuron variability of amplitude and timing was somewhat larger than the trial-to-trial variability, with standard deviations of 1.45 mV and 1.78 ms, respectively, but demonstrating that precise inhibitory control of a population of neurons could proceed with millivolt and millisecond resolution. Finally, the through-train sustainability of light-elicited voltage changes was quantitatively examined by comparing the amplitude mean and amplitude variability, and timing variability of the hyperpolarization events elicited by the first five light pulses to those of the last five light pulses in the train (FIGS. 2Di and 2Dii, left side). Little or no difference was seen for any of these statistics between the beginning and end of a train (p>0.10 for all measures, t-test). Identical conclusions held for the λ=200 ms Poisson train with 46 pulses (FIGS. 2Ciii and 2Civ, and FIGS. 2Di and 2Dii, right side). The high temporal and amplitude fidelity of Halo-mediated hyperpolarizations suggests uses for Halo in simulating inhibitory synaptic inputs, with great precision.

Figure 3A:
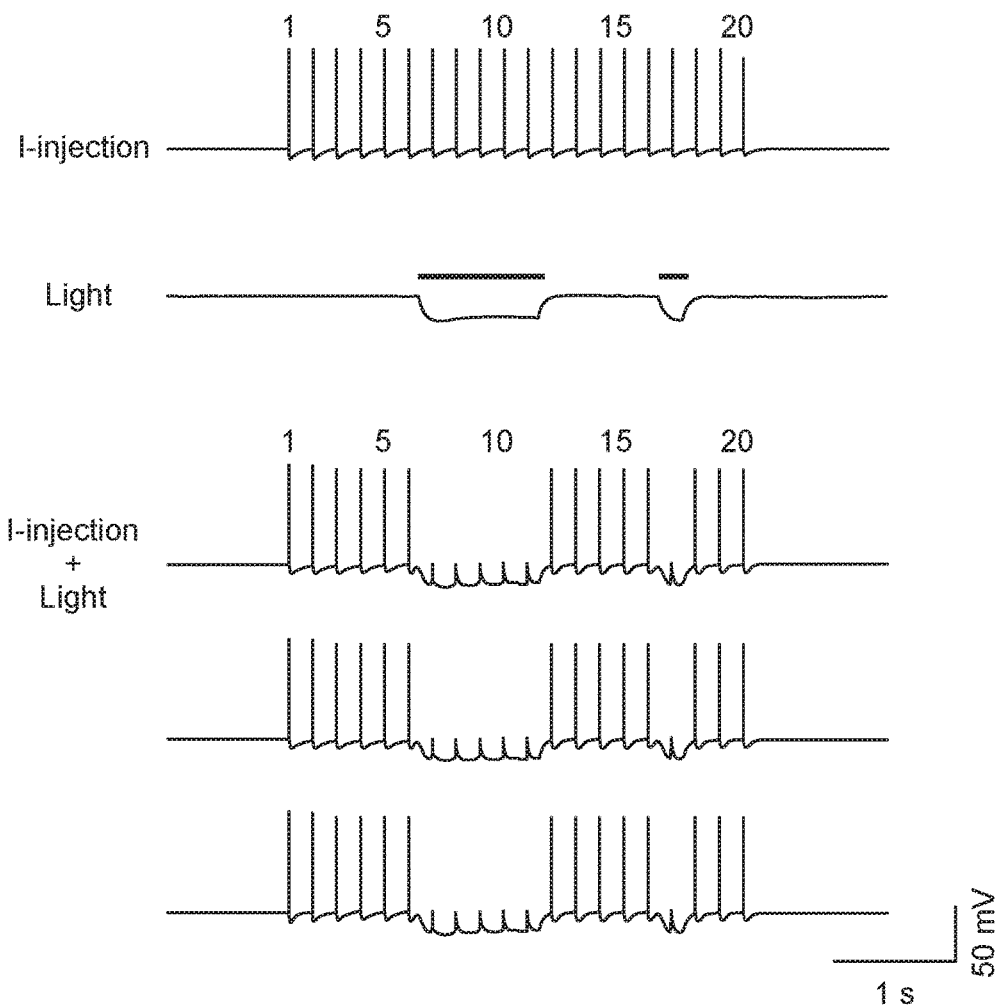
FIG. 3A shows a light-driven spike blockade, demonstrated for a single hippocampal neuron, consistent with an embodiment of the present invention.

FIG. 3 shows reliable and repeatable Halo-mediated neural inactivation, at single-spike temporal resolution. FIG. 3A shows a light-driven spike blockade, demonstrated for a single hippocampal neuron. At the top of FIG. 3A, labeled with "I-injection," neuronal firing of 20 spikes at 5 Hz are induced by pulsed somatic current injection (~300 pA, 4 ms). In the middle of FIG. 3A, labeled with "light," light membrane hyperpolarizations are induced by two periods of yellow light, timed so as to be capable of blocking spikes 7-11 and spike 17 out of the train of 20 spikes. At the bottom of FIG. 3A, labeled as "I-injection+Light", yellow light drives Halo to block neuron spiking (note significant reductions of spikes 7-11 and of spike 17), while leaving spikes elicited during periods of darkness largely intact.

Figure 3B:
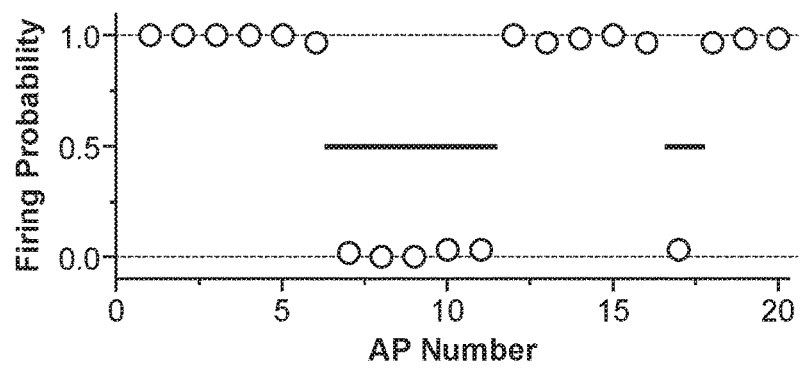
FIG. 3B shows population data (n=6 neurons) for light-driven, Halo-mediated spike blockade, consistent with an embodiment of the present invention.

FIG. 3B shows population data (n=6 neurons) for light-driven, Halo-mediated spike blockade, showing high spike probability during periods of darkness (spikes 1-6, 12-16, and 18-20), and low spike probability during periods of yellow-light illumination (spikes 7-11 and spike 17). Error bars are smaller than the points plotted.

Such experiment were implemented to analyze the ability of Halo to enable rapidly inducible and reversible silencing of neuron spiking. Such ability can be useful to enable time-resolved parsing of the precise neural substrates of behavior. Neurons were intracellularly injected with trains of somatic current pulses (~300 PA, lasting ~4 ms), causing them to fire action potentials at 5 Hz with 100% success rate (FIG. 3A, "I-injection"). Yellow-light pulses were scheduled to occur during the times when certain spikes (i.e., spikes 7-11 and 17) would occur during the somatic current injection protocol (FIG. 3A). The light pulses and the somatic current pulses were presented together (FIG. 3A, "I-injection+light", three trials shown). Spiking was effectively blocked during the periods of yellow-light exposure. The rapid onset and offset kinetics of Halo allowed the deletion of even single spikes. For instance, the second yellow-light pulse, timed for silencing just spike 17, was able to effectively eliminate spike 17 without affecting the firing of spikes 16 or 18 at all. The experiment was repeated five times on each of n=6 neurons (FIG. 3B). During periods when the yellow light was off, it was found that somatic current pulses elicited a spike 98.7% of the time. In contrast, during periods when the yellow light was on, somatic current pulses elicited a spike only 1.2% of the time. The second pulse of yellow light reduced the probability of firing spike 17 to 3.3%, whereas spikes 16 and 18 still fired 96.7% of the time, not significantly different from the spikes at the beginning of the train, before any light exposure at all ($X^2$=1.02, p>0.30). The temporal precision of Halo in silencing spikes therefore offers the possibility of creating ultra-transient (yet precise and effective) lesions of activity in targeted neurons.

A specific embodiment of the present invention includes the use of one member of the type I opsin family, Channelrhodopsin-2 (ChR2), which has received recent attention for its ability to drive neural excitation in response to pulses of blue light (centered around 470 nm). The ability to drive excitation and inhibition in the same neuron, using two different wavelengths of light, could enable answers to questions for which no current technology permits resolution. For example, synchronous neural activity has been correlated with higher-order functions, such as attention and abnormal patterns of neural synchrony that are associated with certain neurological and psychiatric disorders. The ability to drive a neuron with balanced but randomly varying excitation and inhibition may allow alteration of the precise timing of membrane voltage fluctuations, in principle permitting neural synchronization or desynchronization without any side effects, such as alteration of spike rate. This may open up new experiments in testing the causal role of neural synchrony in behavior and pathology.

Figure 4A:
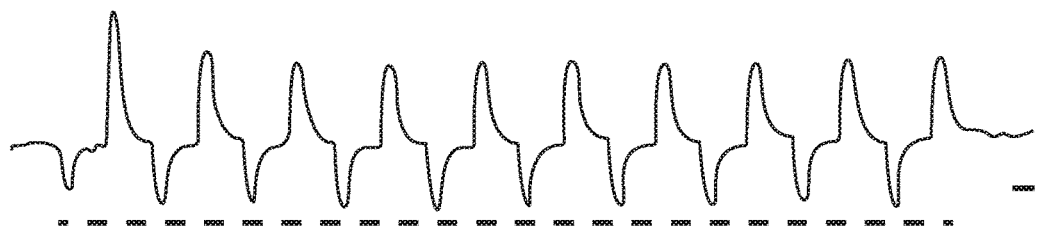
FIG. 4A shows responses of single neurons co-expressing Halo and ChR2, both under control of the CaMKII promoter, to rapidly-switched pulses of yellow and blue light, consistent with an embodiment of the present invention.
Figure 4B:
FIGS. 4B-4D show poisson trains of rapidly-alternating yellow and blue light pulses elicited rapidly-alternating hyperpolarizations and depolarizations in the same neuron, consistent with an embodiment of the present invention.
Figure 4C:
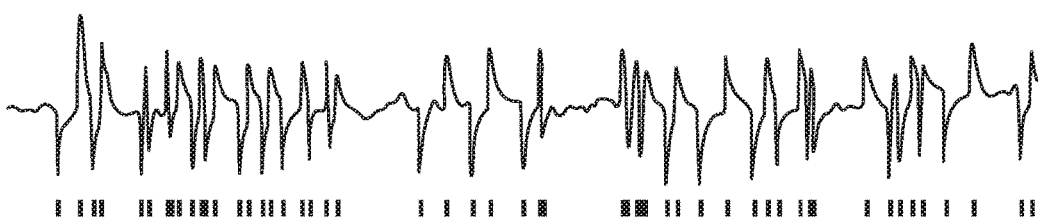
Figure 4D:
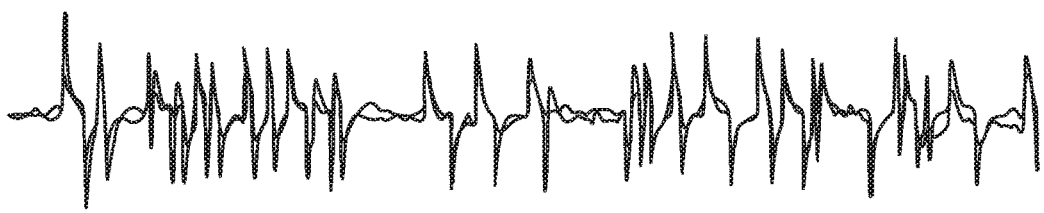

Single neurons co-expressing Halo and ChR2, both under control of the CaMKII promoter, were implemented to allow for response to rapidly-switched pulses of yellow and blue light with hyperpolarizations and depolarizations, respectively (FIG. 4A). Poisson trains ($\lambda$=100 ms) of rapidly-alternating yellow and blue light pulses elicited rapidly-alternating hyperpolarizations and depolarizations in the same neuron (FIG. 4B). In one experiment, the same Poisson train was played back twice with the first train beginning on a blue pulse (FIG. 4B) and the second train beginning on a yellow pulse, (FIG. 4C) so that in the second trace, depolarizations were converted into hyperpolarizations and vice versa. In principle, these traces should be quite similar, but with inverted voltage scale. Indeed, FIG. 4C shows an inverted trace superimposed over the trace in FIG. 4B. The degree of superposition suggests that this approach may indeed be a viable method for high-fidelity, bi-directional control of neural activity at the millisecond timescale (FIG. 4D).

The inhibition provided by Halo is strong enough to silence neurons firing spikes in response to significant intracellular somatic current injections (FIG. 3), yet the photocurrents can appear and disappear within 10-15 milliseconds of light onset and offset, respectively (FIG. 1). Furthermore, the amplitude and timing of responses is reliable from trial to trial, and the amplitude of the voltage changes induced by pulses of yellow light does not detectably run down over time (FIG. 2). The use of Halo can be particularly useful for a number of reasons. For example, the timescale of inducing of and subsequent release of voltage inhibition by Halo is relatively fast.

According to another embodiment of the present invention, Halo is used without ChR2. Millisecond pulses of light can be used with Halo-expressing cells to induce hyperpolarizations of several millivolts, and therefore, may be useful for simulating background or well-timed synaptic activity. Studying the function of not only specific cell types, but specific classes of inhibitory synapse, can be accomplished by creating fusion proteins in which Halo is targeted to specific locations where inhibitory synapses uniquely cluster, such as the axon initial segment.

The ability to functionally lesion brain regions or cell types in a rapidly reversible fashion opens up a large class of experiments in which specific neuron populations must be inactivated for precise, sub-second durations during a task. ChR2, another type I opsin which obligately requires all-trans-retinal for its function, has been shown to function in slices of mammalian brain tissue, or even in the central nervous system in vivo, without needing any chemical supplementation. Therefore, it is believed that no supplementation will be needed for Halo in the intact mammalian brain and in brain slice experiments. Other labs working on classical neural model organisms such as *Drosophila* and *C. elegans* have devised ways of delivering all-trans-retinal to the nervous systems of such animals in order to enable ChR2 function, and thus, it is likely that these retinal-delivery protocols would also work for enabling Halo function in these invertebrates.

The ability to study the causal role of neural synchrony in behavior, neural computation, and neural pathology may be a particularly significant role for ChR2 and Halo, working in concert. The newly-enabled power to drive both excitation and inhibition of genetically-targeted neurons with blue and yellow light seems to be particularly valuable for probing synchrony by utilizing multiple wavelengths to perform both excitation and inhibition in the same specimen. The ability to synchronize and desynchronize neurons by balanced, yet random, patterns of excitation and inhibition may open up new horizons into understanding the causal role of neural synchrony in brain function and disease, an area of longstanding, yet growing, interest.

Optical methods for altering neural circuit function have appeal in part because in principle they can use technology developed for brain imaging. The ability to use optical fibers to image deep neural circuits, for example, also enables the stimulation of deep brain structures. Two-photon excitation methods may prove valuable for driving opsin activities, up to 1 mm deep. Another key aspect of optical methods of neural control is the speed with which activation and inactivation can take place, since it is trivial to modulate light intensity at high speeds, faster than most physiologically relevant processes. Nevertheless, non-optical and chemical approaches will continue to find many powerful uses for reliable, enduring inhibition of specific brain circuits and cell types, especially when large regions of deep brain tissue are involved.

From a neuroengineering standpoint, optical prosthetics capable of inhibiting neural activity may present less-invasive strategies for treating disorders of neural hyperactivity. ChR2 has already proven to be well-tolerated in intact mammalian neural circuits for up to a year. If Halo gains a similar track record, it is possible that Halo-enabled prosthetics may open up new horizons in controlling disorders of excitable cells, such as epilepsy, depression, neuropathic pain, and cardiac hyperexcitability. In the immediate future, the ability to study the effects of well-timed neuron or circuit inactivation in animal models of disease will rapidly reveal new principles for selecting neural circuit targets for treatment of specific disorders. There are also implications of the use of Halo in biotechnological scenarios, such as high-throughput drug screening. Several proposals (and even commercially-available systems) exist for using electrical stimulation to activate excitable cells, thus facilitating the screening of depolarization-gated ion channels. The discovery of drugs that target hyperpolarization-activated channels, such as the family of channels mediating the hyperpolarization-activated cation currents I(h) and I(f), may be useful for identifying possible drugs for tackling problems such as absence seizures, bradycardia, and other disorders. An all-optical method for screening for such drugs, which uses light of one frequency to drive inhibition, and light of another frequency to observe changes in fluorescence of an ion-sensitive chemical or genetically encoded sensor, may revolutionize this process. Thus, Halo not only presents a number of unique features that enable effective, and rapidly inducible and reversible, inhibition to be applied to a number of neural circuit questions, but may open up new horizons in biotechnology as well.

An experimental hippocampal neuron culture, transfection, and survival assay was implemented according to the following methods. Hippocampal regions CA3-CAI of postnatal day 0 or day 1 Sprague-Dawley rats (Charles River) were isolated and treated with trypsin (1 mglml) for 12 minutes. Digestion was stopped by Hanks solution supplemented with 20% fetal bovine serum and trypsin inhibitor. Tissue was dissociated with silicone-coated Pasteur pipettes and centrifuged at 1000 rpm at 4° C. for 10 minutes. Dissociated neurons were plated on glass coverslips precoated with Matrigel (BD Biosciences) at a rough density of approximately two hippocampi per 24 coverslips. Neurons were transfected using a commercially available calcium phosphate transfection kit (Invitrogen), at 3-5 days in vitro. GFP fluorescence was used to identify successfully-transfected neurons, indicating a net transfection efficiency of ~7%. All images and electrophysiological recordings were made on 9-15 day-in-vitro neurons (approximately 4-10 days after transfection). Confocal images of transfected neurons were taken with a Zeiss LSM 510 confocal microscope. Cell death count was carried out on living cultures, seven days after transfection, by adding 4 µM ethidium homodimer-1 (Invitrogen) to the culture medium for 10 minutes at 37° C., then washing the cells with Tyrode's solution (see below). GFP-positive and negative neurons were counted for positive and negative ethidium fluorescence, in five regions on each of three coverslips for this viability assay.

An experiment regarding electrophysiology and optical methods was implemented according to the following methods. Whole cell patch clamp recording was made on 9-15 day-in-vitro neurons using a Multiclamp 700B amplifier, connected to a Digidata 1440 digitizer (Molecular Devices) attached to a PC running pClamp 10. During recording, neurons were bathed in Tyrode's solution containing (in mM) 138 NaCl, 2.4 KCl, 2 CaCl, 2 MgCl, 10 HEPES, 10 Glucose, 24 sucrose, 10 µM NBQX, 10 µM gabazine and 50 µM D-APV. Borosilicate glass (Warner) pipettes were filled with a solution containing (in mM) 130 K-Gluconate, 7 KCl, 2 NaCl, 1 MgCl2, 0.4 EGTA, 10 HEPES, 2 ATP-Mg, 0.3 GTP-Tris and 20 sucrose. Pipette resistance was ~6 M'Ω, and the access resistance was 10-25 M'Ω, which was monitored throughout the voltage-clamp recording. Resting membrane potential was 52-70 mV in current-clamp recording.

Photocurrents were first measured with pairs of 1-second long light pulses, separated by periods of darkness lasting 1 second, while holding neurons in voltage clamp at −70 mV, −30 mV and +10 mV to assay the properties of Halo. Light-induced membrane hyperpolarizations were induced by 1 second duration light pulses, separated by periods of 1 second darkness, in neurons current-clamped at resting membrane potential. Light pulse trains were synthesized by custom software written in MATLAB (Mathworks), and then played to the DG-4 light source through a digital-to-analog converter on the Digidata 1440. For the spike-blockade experiment, spikes were first induced via somatic current injection through the patch pipette. Most of the neurons patched easily fired action potentials with 100% probability, in response to ~300 pA current injections (4 ms duration). For each neuron, injected somatic current magnitudes guaranteed 100% firing rate of 20 spikes, at a rate of 5 Hz.

A DG-4 optical switch with 300-W xenon lamp (Sutter Instruments) was used to deliver all light pulses, for Halo or ChR2 activation. A Texas Red filter set (Chroma, excitation 560/55, diachronic 595LP, emission 645/75) was used to deliver yellow light to activate Halo. The same diachronic mirror was also used to deliver blue light, but with an excitation filter 480/40 in the DG-4, to allow ChR2 excitation. Note that the DC595LP dichroic mirror only reflects 35% of incident 460-500 nm light through the objective; custom-coated dichroics that reflect light all the way into the ultraviolet (as are available from companies such as Chroma) would be optimal.

According to one embodiment of the present invention, the survival replication, differentiation, or death of cells is modulated by electrical activity from Halo. With appropriate light pulses, Halo-expressing cells can be guided down any one of these pathways, depending on the precise pattern of stimulation used to drive activation of Halo. A specific electrical activity pattern results in a specific pattern of downstream signal transduction and in a specific cellular fate response. Therefore, targeting Halo to specific cells, then exposing them to particular light patterns, enables them to be optically driven towards survival, differentiation, replication, or death. This has many potential applications.

For example, in the case where the target cell is a stem cell, particular patterns of activity will drive the replication or differentiation of stem cells (including human embryonic stem cells), or drive the death of the stem cells (in the case where excessive replication is desired to cease). If the target cells are tumor or cancer cells, then targeting Halo to those cells will permit the use of specific and appropriate patterns of light to drive activity, and thus kill the tumor or cancer cells. If the target cells are immune cells, then silencing the cells can prevent the calcium waves that insure cell survival, and reduce the prevalence of autoimmune disease.

Other target cells of this kind may include secretory or organ cells or their precursors, cardiac or other muscle cells, or glial cells in the brain. In each of these cases, it is desirable to control the replication, differentiation, and death of these cells precisely. Halo will be useful for controlling these things in vitro, in vivo in experimental animals, or in vivo in humans (before or after transplantation into the body)—wherever light can be delivered, such as through the skin, via small LEDs, or lasers, or through optical fibers or thin optical endoscopes.

Screening for drugs that modulate ion channel function (e.g., blocking or facilitating ion channel function) can be accomplished using Halo to screen for drugs that modulate ion channel function. One embodiment involves one or more of the following steps:
1) stably express Halo in a cell line;
2) stably express an ion channel of interest ("channel n") in the same cell line;
3) label the cells with a voltage sensitive dye (or other indicator, see below);
4) expose said cells to light, and record the fluorescence of the voltage sensitive dye;
5) expose said cells to a candidate compound that monitors the function of channel n; and
6) expose said cells to light a second time, and record the fluorescence of the voltage sensitive dye.

If the fluorescence is greater during step 6) than step 4), then the candidate drug facilitates channel function. If the fluorescence is smaller during step 6) than step 4), then the candidate drug diminishes channel function. If the fluorescence is equal in steps 4) and 6) (allowing for any bleaching of the dye), then the drug does not affect channel function. In this way, drugs that affect channel function can be detected extremely rapidly.

Steps 1) and 2) of the above process may take several hours or days, but the resulting cell line then suffices for the screening of many (perhaps millions of) drugs, which modulate channel n. Steps 3), 4), 5), and 6) take only a few seconds each; preferably, steps 4), 5), and 6) each take less than 1 second. Steps 4), 5), and 6) take place in a robotic device that moves a 96- or 384-well plate into the focus of an optical beam (see the last section for details on devices). The wells of the plate would all contain the same cell line, in order to facilitate the screening of drugs that affect a particular channel, or each well would contain cells of a different cell line, in order to facilitate the screening of one drug against many different channels ("screening against side effects," see below).

Step 3 can include the use of a voltage-sensitive dye for fast kinetics; however, another dye (e.g., a calcium-sensitive dye in the case that channel n is a calcium channel) could also serve to indicate whether channel function is modulated by the drug. Genetically encoded indicators of voltage or calcium would also be useful for reading out the activity of the cell (e.g., FLASH, GCaMP2, cameleon, etc.). In this case, these indicators would be stably expressed in the cell line as well. Other methods of reading out whether the drug had an effect could also be useful for supplementing this readout (e.g., immunostaining for the phosphorylation of a site that is phosphorylated during or after periods of ion channel activity).

Blindness and other sensory deficits affect millions of people worldwide, severely impacting their quality of life. Halo can be targeted to somatic cells in the human patient to provide a type of sensory prostheses. For example, some forms of blindness destroy photosensor function but leave signal processing in downstream neurons intact. In such diseases, such as macular degeneration or retinitis pigmentosa, targeting Halo to the "off" retinal ganglion cells (e.g., by injecting viruses expressing Halo into the retinal cell layers inside the eye) would enable restoration of visual function. As light increases in the environment, Halo would inhibit the "off" cells, causing increased visual responses in the brain. In such patients treated with Halo targeted to retinal ganglion cells, the retinal ganglion cells would themselves become photosensitive, enabling vision with resolution comparable to the native eye, and not requiring invasive technology beyond that point. Halo is sufficiently sensitive to detect sunlight (power ~1 kW/m$^2$), with maximal sensitivity in the part of the spectrum that is greatest in sunlight. Expressing Halo in a retinal cell, accompanied with a projection device that would amplify the ambient light, would enable vision inside or in lowlight conditions.

Another implementation of Halo involves situations where the central nervous system neurons in a person are infected with virus expressing Halo (or otherwise come to express Halo). These neurons would then be inhabitable by pulses of yellow light. This gene therapy approach would therefore allow optical inhibition of precise neuronal targets in the brain. If the targeted neurons are epileptic, this would enable silencing of those cells without needing ablative surgery. If the targeted neurons were in the frontal cortex or other parts of the brain, these light-sensitive neurons would permit optical modulation of emotion or cognition. If the targeted neurons were in the spinal cord, neurons that mediate pain stimuli could then be inhibited by light.

In general, such a gene therapy approach opens up a new kind of generalized prosthetic in defined parts of the nervous system. The prosthetic allows light to be converted into neural activity.

In another instance, Halo is targeted to specific and different parts of a cell. For example, targeting Halo to the axon hillock using the AIS (axon initial segment) targeting sequence allows more powerful inhibition. Fusing Halo to a targeting sequence of DNA, so that the resultant protein contains both Halo and the targeting peptide, allows Halo to be sent to the presynaptic terminal, the postsynaptic terminal, the nucleus, or other intracellular compartments. Such targeting sequences include PDZ domains, glutamate and GABA receptor C-terminal sequences, ion channel C-terminal sequences, presynaptic scaffolding targeting sequences, and other targeting sequences. These versions of Halo can then be used to trigger specific intracellular signaling events, including those important for neuroprotection, memory, or other enduring signaling functions.

In a combinatorial fashion, these reagents could complement the other applications of Halo. For example, these reagents could be useful for drug screening (e.g., finding drugs that modulate the function of a channel in a particular subcellular compartment). These reagents could also be useful for prosthetic devices (e.g., driving activity on the dendrites of a neuron, to more closely mimic natural synaptic activity).

Various embodiments, including but not limited to those involving drug screening, employ an optical imaging device containing 1) a light source (LED, lamp, laser) for illuminating the cell expressing Halo and driving a change in cell voltage, 2) a light source for illuminating a dye or indicator, possibly the same light source as used for driving the voltage change, and 3) a switch for alternating between the two light sources or a beamsplitter for simultaneous non-interfering delivery of both kinds of light. The fluorescence of the dye or indicator would be measured by a sensor (CCD camera, PMT, or photodiode). This kind of device can be useful for ion channel drug screening, as described above. The device itself consists of a robotic arm for moving a plate (e.g., a 384-well plate) through the arena where the light sources and sensor are present.

In one embodiment, diagnostic applications, as mentioned herein, use a combined light source imaging device. For example, taking cells from a patient, expressing Halo in them, and then exposing them to light, can be used to reveal patient-specific ion channel syndromes in biopsy samples or in cells of the circulatory system.

For various implementations, an implantable or head-mounted LED, or other small light source can be used. Such a light source can be implanted under the skin, under the skull, deep within the brain, or deep within another organ of interest, in which Halo-expressing cells are also located (either exogenously introduced, or endogenously located and targeted with a virus). This device can be used for stimulating Halo in cells located directly adjacent to the light source. A strip of LEDs, each individually controllable, is useful. For the example of the cortical implant, a 2-dimensional array of LEDs is useful.

For medical applications, various embodiments have LEDs that are remotely powered. A remotely-powered LED can be made, for example, by combining an LED in a closed-loop series circuit with an inductor. This would allow radiofrequency (RF) energy or rapidly changing magnetic fields (e.g., delivered by a transcranial magnetic resonance (TMS) coil) to temporarily power-up the inductor, and thus the connected LED, allowing local delivery of light, even deep in a brain structure. In certain embodiments, such a device is implanted under the skin, under the skull, deep within the brain, or deep within another organ of interest in which Halo-expressing cells are also located (either exogenously introduced, or endogenously located and targeted with a virus). Optionally, another device is used to remotely deliver RF or magnetic energy (e.g., placed nearby or worn on the patient) for activating the implanted device.

N. pharaonis halorhodopsin with mammalian-optimized codon usage was synthesized as a DNA sequence according to the sequence listing provided on the following page as Sequence Listing A.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use of digital logic or microprocessors to control the emitted light. Such modifications and changes do not depart from the true spirit and scope of the present invention, which is set forth in the following claims.

SEQUENCE LISTING A

The N. pharaonis halorhodpsin with mammalian-optimized codon usage was synthesized according to the following DNA sequence (876 base pairs).

ATGACTGAGACCCTCCCACCCGTGACTGAAAGCGCCGTCGCTCTGCAAGC

AGAGGTTACCCAGCGGGAGCTGTTCGAGTTCGTCCTCAACGACCCCCTCC

TGGCTTCTAGCCTCTACATCAACATTGCTCTGGCAGGCCTGTCTATACTG

CTGTTCGTCTTCATGACCAGGGGACTCGATGACCCTAGGGCTAAACTGAT

TGCAGTGAGCACAATTCTGGTTCCCGTGGTCTCTATCGCTTCCTACACTG

GGCTGGCATCTGGTCTCACAATCAGTGTCCTGGAAATGCCAGCTGGCCAC

TTTGCCGAAGGGAGTTCTGTCATGCTGGGAGGCGAAGAGGTCGATGGGGT

TGTCACAATGTGGGGTCGCTACCTCACCTGGGCTCTCAGTACCCCCATGA

TCCTGCTGGCACTCGGACTCCTGGCCGGAAGTAACGCCACCAAACTCTTC

ACTGCTATTACATTCGATATCGCCATGTGCGTGACCGGGCTCGCAGCTGC

CCTCACCACCAGCAGCCATCTGATGAGATGGTTTTGGTATGCCATCTCTT

GTGCCTGCTTTCTGGTGGTGCTGTATATCCTGCTGGTGGAGTGGGCTCAG

GATGCCAAGGCTGCAGGGACAGCCGACATGTTTAATACACTGAAGCTGCT

CACTGTGGTGATGTGGCTGGGTTACCCTATCGTTTGGGCACTCGGCGTGG

AGGGAATCGCAGTTCTGCCTGTTGGTGTGACAAGCTGGGGCTACTCCTTC

CTGGACATTGTGGCCAAGTATATTTTTGCCTTTCTGCTGCTGAATTATCT

GACTTCCAATGAGTCCGTGGTGTCCGGCTCCATACTGGACGTGCCATCCG

CCAGCGGCACACCTGCCGATGACTGA).

The Halo-GFP fusion protein was generated by PCR amplification of the Halo gene with primers 5' GAATTCGC-CACCATGACTGAGACCCTCCCACCCGTG and 3'GGATCCGTCATCGGCAGGTGTGCCGCTGGC and inserted into the EcoRI and BamHI cites of pEGFP-N3 (Clontech), which has the CMV promoter. The Halo-GFP fusion protein sequence was then PCR amplified with primers 5'CCGGTGCCACCATGACTGAGACCCTCCCAC-CCGTG and 3'GAATTCTTACTTGTACAGCTCGTC-CATCGG and inserted into lentiviral vector FCK(1.3)GW containing the CaMKII promoter via AgeI and EcoRI sites. All constructs were verified by sequencing. The channel-rhodopsin construct used in various experiments, FCK-hCmC, contains the human/mammalian codon-optimized gene ChR2 fused to fluorescent protein mCherry, under the CaMKII promoter.

What is claimed is:

1. A method for screening a candidate agent that modulates ion channel function in a mammalian cell, the method comprising:
   (i) expressing in a mammalian cell a light-driven chloride ion pump from *Natronobacterium pharaonis* (NpHR);
   (ii) expressing in the mammalian cell an ion channel;
   (iii) labeling the mammalian cell with a voltage sensitive dye;
   (iv) exposing the mammalian cell to a first light;
   (v) recording a first fluorescence signal of the voltage sensitive dye;
   (vi) exposing the mammalian cell expressing NpHR to the candidate agent;
   (vii) exposing the mammalian cell expressing NpHR to a second light; and
   (viii) recording the second fluorescence signal of the voltage sensitive dye, and
   wherein if the second fluorescence signal of the voltage sensitive dye is greater than the first fluorescence signal of the voltage sensitive dye, then the candidate agent facilitates ion channel function.

2. The method of claim 1, wherein if the first fluorescence signal of the voltage sensitive dye is equal to the second fluorescence signal of the voltage sensitive dye, the candidate agent does not have an affect ion channel function.

3. The method of claim 1, wherein if the second fluorescence signal of the voltage sensitive dye is smaller than the first fluorescence signal of the voltage sensitive dye, than the candidate agent diminishes ion channel function.

4. The method of claim 1, wherein the ion channel is a Channelrhodopsin-2 (ChR2) ion channel.

5. The method of claim 4, wherein the first light is a yellow light or a blue light, wherein the yellow light activates the NpHR ion pump expressed in the mammalian cell and the blue light activates the ChR2 ion channel expressed in the mammalian cell.

6. The method of claim 1, wherein the voltage sensitive dye is a calcium-sensitive dye.

7. The method of claim 1, wherein the second light is a yellow light or a blue light, wherein the yellow light activates the NpHR ion pump expressed in the mammalian cell and the blue light activates the ChR2 ion channel expressed in the mammalian cell.

* * * * *